(12) United States Patent
Lee et al.

(10) Patent No.: US 8,507,281 B2
(45) Date of Patent: Aug. 13, 2013

(54) METHOD OF REMOVING ABNORMAL DATA AND BLOOD COMPONENT SPECTROSCOPY ANALYSIS SYSTEM EMPLOYING THE SAME

(75) Inventors: Jong-youn Lee, Yongin-si (KR); Gil-won Yoon, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 1783 days.

(21) Appl. No.: 10/753,218

(22) Filed: Jan. 7, 2004

(65) Prior Publication Data

US 2004/0204865 A1   Oct. 14, 2004

(30) Foreign Application Priority Data

Jan. 7, 2003   (KR) .................. 10-2003-0000779

(51) Int. Cl.
   *G01N 33/49*   (2006.01)
(52) U.S. Cl.
   USPC .................. 436/63; 436/11; 436/16; 436/15; 436/164; 422/82.05; 702/19; 702/25; 702/66
(58) Field of Classification Search
   USPC .............. 422/82.05; 436/11, 16, 15, 63, 164; 702/19, 25, 66
   See application file for complete search history.

(56) References Cited

U.S. PATENT DOCUMENTS

| | | | |
|---|---|---|---|
| 5,025,791 A | 6/1991 | Niwa | |
| 5,285,782 A | 2/1994 | Prosser | |
| 5,517,988 A | 5/1996 | Gerhard | |
| 5,553,615 A * | 9/1996 | Carim et al. | 600/324 |
| 5,645,060 A | 7/1997 | Yorkey | |
| 5,842,979 A * | 12/1998 | Jarman | 600/322 |
| 5,983,122 A * | 11/1999 | Jarman et al. | 600/323 |
| 6,393,311 B1 | 5/2002 | Edgar, Jr. et al. | |
| 6,496,723 B1 | 12/2002 | Kawachi et al. | |
| 2001/0008953 A1 | 7/2001 | Honda et al. | |

FOREIGN PATENT DOCUMENTS

| | | |
|---|---|---|
| JP | 63-034731 | 2/1988 |
| JP | 09-113309 | 5/1997 |
| JP | 2001-061795 | 3/2001 |
| JP | 2001-190510 | 7/2001 |
| WO | WO 88/01128 A2 | 2/1988 |

* cited by examiner

*Primary Examiner* — Lyle Alexander
(74) *Attorney, Agent, or Firm* — Lee & Morse, P.C.

(57) ABSTRACT

A method of removing abnormal data in a blood component analysis system using spectroscopy to estimate a concentration of a blood component by analyzing a photo-plethysmographic (PPG) signal obtained by radiating light of first and second wavelengths reacting to the blood component on a subject and detecting light corresponding to the first and second wavelengths output from the subject, includes collecting the PPG signal corresponding to the first and second wavelengths for a predetermined unit period of time, calculating "n" parameters, with respect to "n" pulse data included in the collected PPG signal, where n is a positive integer, calculating an average of the "n" parameters, and comparing a ratio of a number of parameters whose deviation from the average is greater than a predetermined standard deviation to the "n" parameters with a predetermined removal reference value to determine whether the "n" pulse data is valid.

16 Claims, 4 Drawing Sheets

METHOD OF REMOVING ABNORMAL DATA AND BLOOD COMPONENT SPECTROSCOPY ANALYSIS SYSTEM EMPLOYING THE SAME

BACKGROUND OF THE INVENTION

1. Field of the Invention

The present invention relates to a blood component analysis system. More particularly, the present invention relates to a method of removing abnormal data generated due to internal and external factors, and to a blood component spectroscopy analysis system employing the same.

2. Description of the Related Art

The measurement of a vital signal using a non-invasive method is an important issue in the field of current medical engineering, and methods of measuring various physiological variables have been developed. In particular, various approaches for analyzing blood components without collecting blood have been published, and studies on analysis of blood components without collecting blood have been undertaken. For example, in a method of analyzing blood components using spectroscopy, without collecting blood, a patient does not suffer pain and is not exposed to potential infection, and the result of analysis can be obtained in real time. Due to these advantages and the development of related technology, generalized techniques for conventional equipment for measuring an oxygen saturation have been applied to medical instruments for analyzing blood components such as hemoglobin and glucose. Such medical instruments use a method of analyzing a blood component by measuring a difference in an amount of light of different wavelengths absorbed by a human body using light having a specific wavelength reacting with the blood component.

A photo-plethysmographic (PPG) signal generated when spectroscopy is used includes a pulsatile component and a non-pulsatile component. The PPG signal will be described in detail with reference to FIG. 1. In FIG. 1, "Io" denotes an amount of light radiated to a human body, "It" denotes an amount of light passing through the human body, "Ia" denotes an amount of light absorbed by the human body, "To" denotes a heart beat period, "Ip" denotes a maximum point of a pulsatile component, "Iv" denotes a minimum point of the pulsatile component, "P1" denotes a variation of light intensity due to the pulsatile component, i.e., an alternating current (AC) component, and "P2" denotes a variation of light intensity due to a non-pulsatile component, i.e., a direct current (DC) component. Components absorbing the light radiated to the human body are largely divided into non-pulsatile components, i.e., "P2" components such as bones and vital tissue which do not change with time, and arterial pulsatile components, i.e., "P1" components which change with time due to heart beats.

Accurately measuring the amount of light absorbed by the pulsatile components changing with time is essential to a method of analyzing a blood component using a ratiometric. However, the amplitude and the base line of the PPG signal frequently change according to internal factors, such as breathing, blood pressure, pulse rate, body temperature, a state of blood vessels, or an autonomic nervous system, and to external factors such as spontaneous or non-spontaneous motion. In quantitative terms, as compared to the amount of light absorbed by a non-pulsatile component, typically the amplitude of a pulsatile component changes within a range of 2 through 5%, and the base line of the PPG signal changes within a range of 3 through 5%. These changes in the amplitude of the pulsatile component and the base line of the PPG signal due to an internal factor causes abnormal data. As a result, errors occur in the analysis of a blood component using spectroscopy.

Current techniques remove abnormal data generated only due to external factors, such as motion-induced noise and an unstable contact of a probe, in a system for measuring oxygen saturation. Further, many current techniques require separate hardware to measure the external factors. Finally, in these current techniques, a physiological signal such as an oxygen saturation signal is measured after a predetermined time has passed until a patient becomes physiologically stable, and therefore, a lengthy measuring time is required.

SUMMARY OF THE INVENTION

It is a feature of the present invention to provide a method of removing abnormal data generated due to both internal and external vital factors, such as motion-induced noise or an unstable contact of a probe, in a blood component spectroscopy analysis system.

It is also a feature of the present invention to provide a blood component spectroscopy analysis system employing the above-described removal of abnormal data so that the accuracy of analysis is increased and the measurement time is reduced.

At least one of the above and other features of the present invention may be realized by providing a method of removing abnormal data in a blood component analysis system using spectroscopy to estimate a concentration of a blood component by analyzing a photo-plethysmographic (PPG) signal obtained by radiating light of first and second wavelengths reacting to the blood component on a subject and detecting light corresponding to the first and second wavelengths output from the subject, the method including (a) collecting the PPG signal corresponding to the first and second wavelengths for a predetermined unit period of time, (b) calculating "n" parameters, with respect to "n" pulse data included in the collected PPG signal, where n is a positive integer, (c) calculating an average of the "n" parameters, and (d) comparing a ratio of a number of parameters whose deviation from the average is greater than a predetermined standard deviation to the "n" parameters with a predetermined removal reference value to determine whether the "n" pulse data is valid.

The method may include updating all or at least one of the "n" pulse data and repeating steps (b) through (d) when the ratio is equal to or greater than the predetermined removal reference value in step (d).

In the method, the standard deviation may be determined according to the first and second wavelengths. When the first and second wavelengths correspond to an isobestic point, the standard deviation may be set to ±3.5% through ±4.5%. When the first and second wavelengths are in one of a red range and an infrared range, the standard deviation may be set to ±1.5% through ±2.5%.

The "n" pulse data may be generated from a modulated signal influenced by a change in a blood flow caused by an external pressure.

The method may further include storing the "n" pulse data when the ratio is less than the predetermined removal reference value in step (d).

At least one of the above and other features may be realized by providing a computer-readable recording medium in a blood component analysis system using spectroscopy to estimate a concentration of a blood component by analyzing a photo-plethysmographic (PPG) signal obtained by radiating light of first and second wavelengths reacting to the blood component on a subject and detecting light corresponding to the first and second wavelengths output from the subject, the computer-readable recording medium including a first program for calculating "n" parameters with respect to "n" pulses included in a PPG signal corresponding to the first and second wavelengths, the PPG signal being collected for a predetermined unit period of time, where n is a positive integer; and a second program for calculating an average of the "n" parameters and comparing a ratio of a number of parameters whose deviation from the average is greater than a predetermined standard deviation to the "n" parameters with a predetermined removal reference value to determine whether the "n" pulse data is valid.

The computer readable recording medium may further include a third program for storing "n" pulse data when the second program determines the "n" pulse data is valid, and updating at least one of the "n" pulse data when the second program determines the "n" pulse data is not valid and iterating the first and second programs for updated data. In the computer readable recording medium, all of the "n" pulse data may be updated.

At least one of the above and other features may be realized by providing a blood component analysis system using spectroscopy, including a light emitter having at least a first light source emitting light of a first wavelength and a second light source emitting light of a second wavelength, each first and second wavelengths reacting to a particular blood component, the first and second light source providing light to a subject, a light receiver for detecting light output from the subject and outputting an electrical signal in response thereto, and a signal processor for extracting a photo-plethysmographic (PPG) signal corresponding to the first and second wavelengths reacting to the particular blood component from the electrical signal, calculating an average of "n" parameters with respect to "n" pulses included in the PPG signal corresponding to the first and second wavelengths, and comparing a ratio of the number of parameters whose deviation from the average is greater than a predetermined standard deviation to the "n" parameters with a predetermined removal reference value to determine whether the "n" pulse data is valid, where n is a positive integer.

The signal processor may include a First In First Out (FIFO) data buffer storing the "n" pulse data, and when the "n" pulse data is determined as being invalid, divides the "n" pulse data into predetermined unit groups, replaces a first predetermined unit group composed of first input data with the same amount of new data as the first predetermined unit group, and determines whether new "n" pulse data is valid.

In the system, the standard deviation may be determined according to the first and second wavelengths. When the first and second wavelengths correspond to an isobestic point, the standard deviation may be set to ±3.5% through ±4.5%. When the first and second wavelengths are in one of a red range and an infrared range, the standard deviation may be set to ±1.5% through ±2.5%.

The "n" pulse data may be generated from a modulated signal influenced by a change in a blood flow caused by an external pressure.

The system may further include a storage unit storing the "n" pulse data determined to be valid. In the system, the signal processor may control a timing of the light emitter.

BRIEF DESCRIPTION OF THE DRAWINGS

The above and other features and advantages of the present invention will become readily apparent to those of skill in the art by describing in detail embodiments thereof with reference to the attached drawings, in which.

DETAILED DESCRIPTION OF THE INVENTION

Korean Patent Application No. 2003-779, filed on Jan. 7, 2003, and entitled: "Method of Removing Abnormal Data and Blood Component Spectroscopy Analysis System Employing the Same," is incorporated by reference herein in its entirety.

Figure 1:
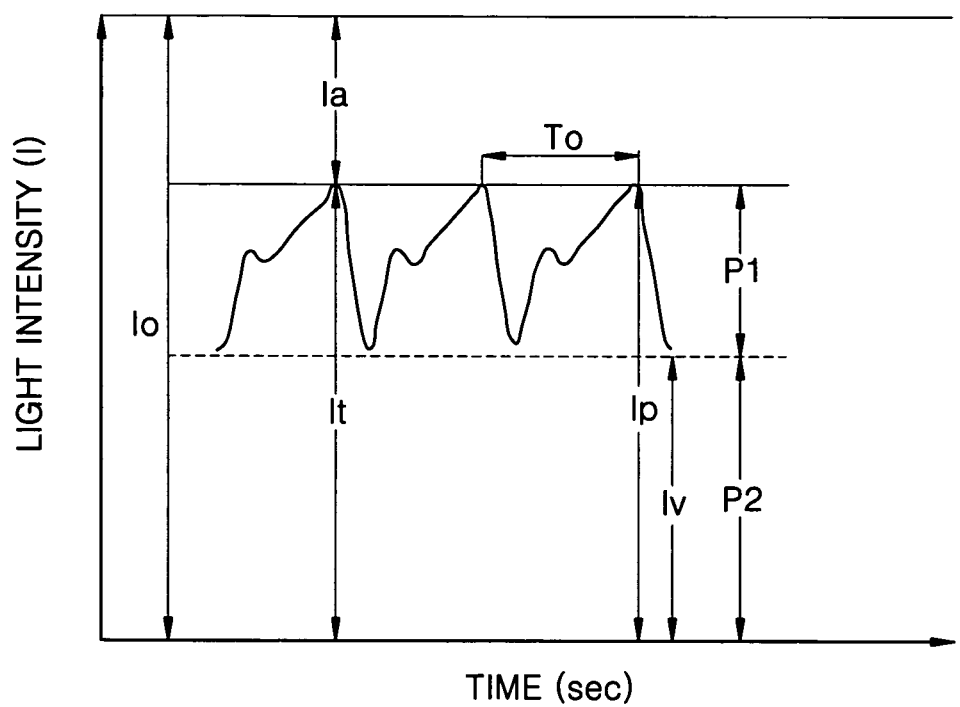
FIG. 1 is a graph illustrating a typical photo-plethysmographic (PPG) signal.
Figure 2:
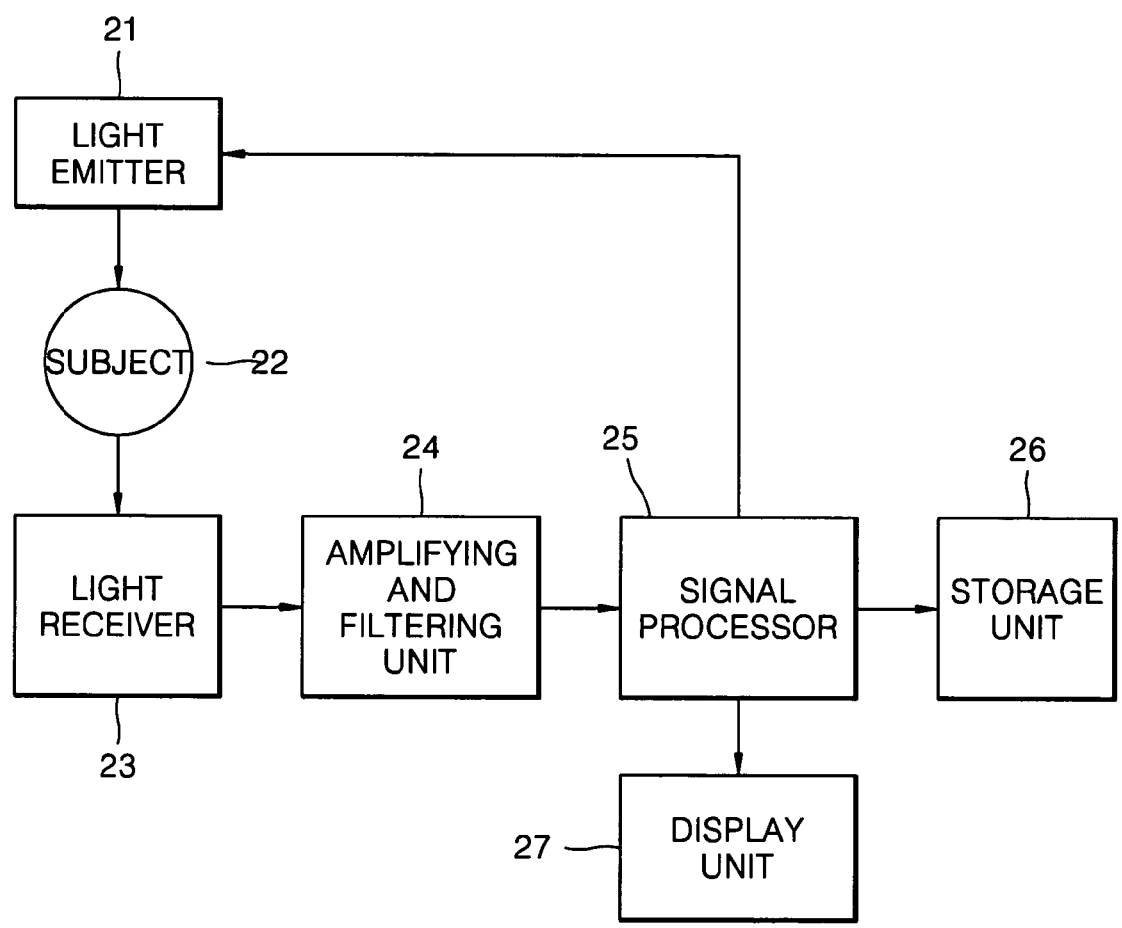
FIG. 2 is a block diagram of a blood component spectroscopy analysis system according to an embodiment of the present invention.

FIG. 2 is a block diagram of a blood component spectroscopy analysis system according to an embodiment of the present invention. The blood component spectroscopy analysis system includes a light emitter 21, a subject 22, a light receiver 23, an amplifying and filtering unit 24, a signal processor 25, a storage unit 26, and a display unit 27.

The light emitter 21 includes at least two light sources, for example, light emitting diodes, each of which emits light of a wavelength reacting to a particular blood component. Each light source radiates light of the particular wavelength to the subject 22 according to timing controlled by the signal processor 25.

The light receiver 23 receives light transmitted, scattered, or reflected from the subject 22 positioned between the light emitter 21 and the light receiver 23, converts the received light into an electrical signal, and provides the electrical signal to the amplifying and filtering unit 24. The amplifying and filtering unit 24 amplifies the electrical signal to a predetermined level and then filters the amplified electrical signal to remove a noise component from the electrical signal.

The signal processor 25 extracts a photo-plethysmographic (PPG) signal reacting to a particular blood component from the electrical signal provided from the amplifying and filtering unit 24, converts the PPG signal into digital data, performs signal analysis and processing on the digital data in order to remove abnormal data therefrom, and provides a signal resulting from the signal processing to the storage unit 26 and the display unit 27. The signal processor 25 includes a computer-readable recording medium in which a program for executing a method of removing abnormal data according to the present invention is recorded. The signal processor 25 may include a data buffer having a First-In-First-Out (FIFO) structure for storing "n" data, where n is a positive integer. Here, when "n" data are determined as being removed as the result of the signal analysis and processing, the "n" data can be divided into a predetermined number of groups, for example, five groups, and only first input n/5 data can be updated and applied to signal analysis for removing abnormal data.

The storage unit 26 stores digital data determined to be valid as the result of the processing of the signal processor 25. The display unit 27 displays the result of the processing of the signal processor 25.

Figure 3:
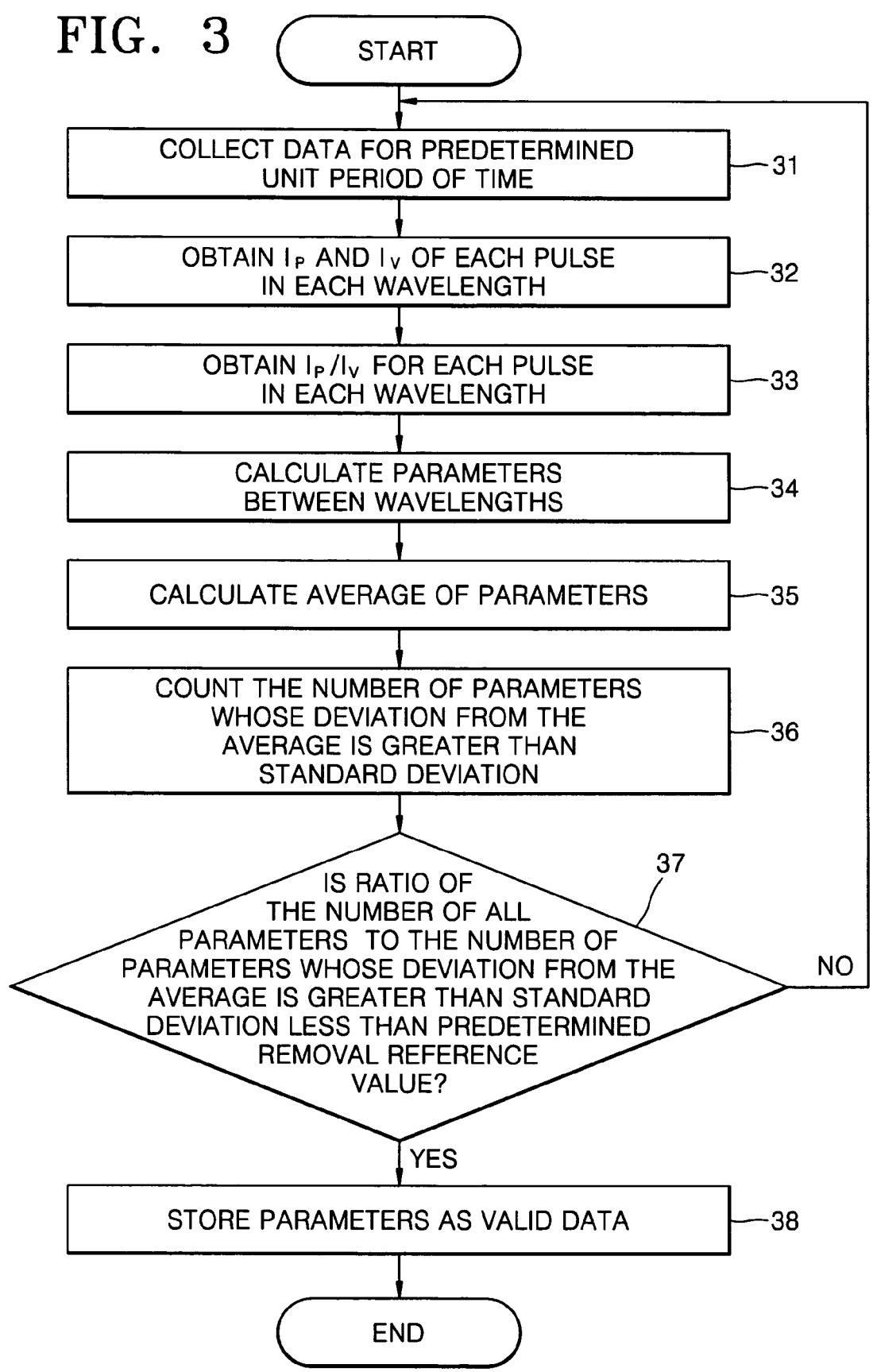
FIG. 3 is a flowchart of a method of removing abnormal data according to an embodiment of the present invention.
Figure 4:
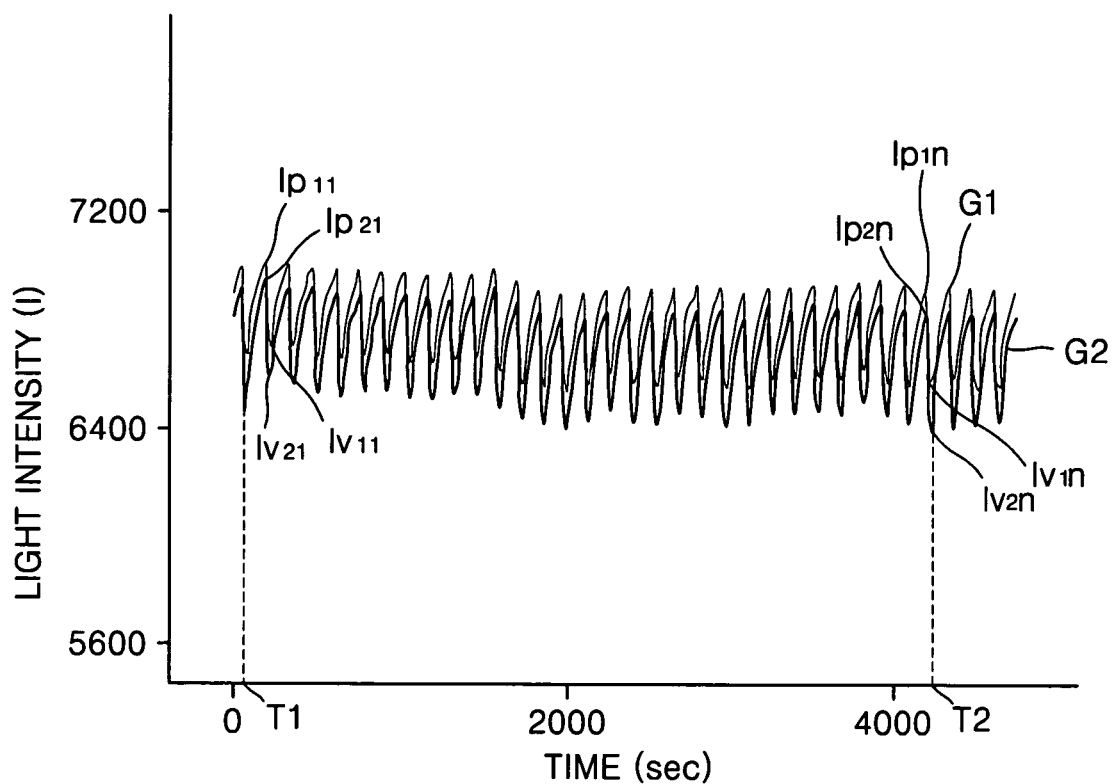
FIG. 4 is an example of a graph showing light intensities of a first wavelength and a second wavelength, which define parameters used in each stage of the method shown in FIG. 3.

FIG. 3 is a flowchart of a method of removing abnormal data according to an embodiment of the present invention. The method includes collecting data (31), calculating an average of parameters between wavelengths (32 through 35), and determining whether the parameters are valid data using the average of the parameters, a standard deviation, and a predetermined removal reference value (36 through 38). The method shown in FIG. 3 will be described with reference to FIG. 4.

Referring to FIG. 3, "n" pulse data of a PPG signal provided from the amplifying and filtering unit 24 are collected according to their wavelengths for a predetermined unit period of time, for example, from T1 to T2, in step 31. The "n" pulse data may usually have a heartbeat period and may be generated from a modulated signal having a large amplitude due to a change in a blood flow caused by an external pressure.

In step 32, a maximum point $I_p$ and a minimum point $I_v$ of light intensity are obtained for each pulse included in the predetermined unit period of time from the pulse data groups collected according to their wavelengths. Graphs G1 and G2 respectively illustrate the light intensity with respect to a first wavelength and a second wavelength, when "n" pulses appear for the time from T1 to T2. The maximum points $I_{p11}$ through $I_{p1n}$ and the minimum points $I_{v11}$ through $I_{v1n}$ of the individual "n" pulses on the graph G1 for the first wavelength are obtained, and the maximum points $I_{p21}$ through $I_{p2n}$ and the minimum points $I_{v21}$ through $I_{v2n}$ of the individual "n" pulses on the graph G2 for the second wavelength are obtained.

In step 33, a logarithmic ratio $\ln(I_p/I_v)$ of the maximum point $I_p$ and the minimum point $I_v$ of each pulse is calculated for each wavelength. More specifically, in the graph G1 for the first wavelength, logarithmic ratios $\ln(I_{p11}/I_{v11})$ through $\ln(I_{p1n}/I_{v1n})$ are calculated for first through n-th pulses. In the graph G2 for the second wavelength, logarithmic ratios $\ln(I_{p21}/I_{v21})$ through $\ln(I_{p2n}/I_{v2n})$ are calculated for first through n-th pulses.

In step 34, the logarithmic ratio $\ln(I_p/I_v)$ obtained for each wavelength is used to calculate a parameter, for example, a ratio of ratios (ROR) between the wavelengths, that is, a ratio $R_{12}$ of the logarithmic ratio $\ln(I_{p1k}/I_{v1k})$ of each pulse in the first wavelength (where k is 1 through n) to the logarithmic ratio $\ln(I_{p2k}/I_{v2k})$ of each pulse in the second wavelength (where k is 1 through n). The ROR $R_{12}$ between the first and second wavelengths may be expressed by Formula (1):

$$R_{12} = \frac{\ln(I_{p1k}/I_{v1k})}{\ln(I_{p2k}/I_{v2k})} \quad (1)$$

In step 35, an average $M_{12}$ of RORs $R_{12}$ between the first and second wavelengths is calculated according to Formula (2):

$$M_{12} = \frac{\sum_{k=1}^{n} \frac{\ln(I_{p1k}/I_{v1k})}{\ln(I_{p2k}/I_{v2k})}}{n} \quad (2)$$

In step 36, among the "n" parameters calculated in step 34, the number "m" of parameters, whose deviation from the average $M_{12}$ calculated in step 35 is greater than a standard deviation, is counted. Here, the standard deviation may be set to an optimal value through experiments or simulations. For example, the standard deviation can be set to be different depending on the type of two wavelengths used to obtain the ROR between wavelengths. When the two wavelengths correspond to isobestic point, the standard deviation is set to ±3.5% through ±4.5% and is preferably set to ±4%. When the two wavelengths are in the red or infrared range, the standard deviation is set to ±1.5% through ±2.5% and is preferably set to ±2%.

In step 37, a ratio of the number "n" of all parameters, which is obtained in step 34, to the number "m" of parameters whose deviation from the average is greater than the standard deviation, which is obtained in step 36, i.e., m/n, is compared with a predetermined removal reference value. Here, the removal reference value may be set to an optimal value through experiments or simulations to ensure the accuracy of analysis. As the result of the comparison in step 37, if the ratio m/n is greater than or equal to the predetermined removal reference value, the currently collected "n" data are discarded and excluded from the analysis, and then the method returns to step 31. Here, in step 31, all of the "n" data may be updated with new "n" data. Alternatively, the "n" data may be divided into predetermined unit groups, a first predetermined unit group composed of first input data is replaced with the same amount of new data as the first predetermined unit group.

If the ratio m/n is less than the predetermined removal reference value, the "n" RORs $R_{12}$ between the first and second wavelengths, which are obtained in step 34, are determined to be valid data and are stored in the storage unit 26. The average of the valid data stored in the storage unit 26, i.e., the average of the RORs $R_{12}$ between the first and second wavelengths, can be used in, for example, a regressive equation obtained through multivariate linear regressive analysis so as to calculate the concentration of the particular blood component.

For example, when a regressive equation for calculating the amount (Hb) of hemoglobin is expressed by Formula (3), examples of the average of the RORs between the first and second wavelengths determined as valid data in steps 31 through 38 are shown in Table 1.

$$Hb = 50.3 - 21.5 \times R_{13} - 1.30 \times R_{15} - 9.00 \times R_{45} \quad (3)$$

TABLE 1

| Pulse index | $R_{13}$ | $R_{15}$ | $R_{45}$ |
|---|---|---|---|
| 1 | 1.11935 | 1.56065 | 1.37540 |
| 2 | 1.13040 | 1.51785 | 1.28079 |
| 3 | 1.11839 | 1.55493 | 1.32513 |
| 4 | 1.15221 | 1.51489 | 1.29946 |
| 5 | 1.16072 | 1.57932 | 1.33420 |
| 6 | 1.15716 | 1.49149 | 1.25697 |
| 7 | 1.19721 | 1.52200 | 1.26801 |
| 8 | 1.09604 | 1.45250 | 1.30688 |
| 9 | 1.08103 | 1.56253 | 1.32151 |
| 10 | 1.11863 | 1.55737 | 1.32719 |
| 11 | 1.11456 | 1.50028 | 1.31471 |
| 12 | 1.17718 | 1.59165 | 1.36132 |
| 13 | 1.13893 | 1.59417 | 1.40585 |
| 14 | 1.11350 | 1.53898 | 1.36942 |
| 15 | 1.11424 | 1.52678 | 1.30636 |
| 16 | 1.18262 | 1.60972 | 1.34542 |
| 17 | 1.18803 | 1.66496 | 1.45322 |
| 18 | 1.17468 | 1.59366 | 1.36323 |
| 19 | 1.17791 | 1.63599 | 1.38658 |
| 20 | 1.12564 | 1.63940 | 1.38449 |
| 21 | 1.15660 | 1.59757 | 1.38367 |
| 22 | 1.12855 | 1.58233 | 1.35407 |
| 23 | 1.11076 | 1.62814 | 1.42659 |
| 24 | 1.19795 | 1.59025 | 1.35692 |
| 25 | 1.16404 | 1.59834 | 1.37347 |
| 26 | 1.12490 | 1.55290 | 1.28225 |
| 27 | 1.12226 | 1.50934 | 1.34515 |
| 28 | 1.16658 | 1.55562 | 1.32509 |
| 29 | 1.13476 | 1.58237 | 1.35572 |
| 30 | 1.10259 | 1.62487 | 1.39802 |
| Average | 1.14158 | 1.56769 | 1.34624 |

Here, the number "n" of pulses included in a predetermined unit period of time is 30, $R_{13}$ denotes an ROR between a wavelength of 569 nm and a wavelength of 805 nm, $R_{15}$ denotes an ROR between a wavelength of 569 nm and a wavelength of 970 nm, and $R_{45}$ denotes an ROR between a wavelength of 940 nm and a wavelength of 970 nm. The concentration of hemoglobin can be estimated by applying the average of RORs between two wavelengths to $R_{13}$, $R_{15}$, or $R_{45}$, the RORs being determined as valid data according to the present invention.

The present invention may be realized as a program recorded on a computer-readable recording medium and may be read by a computer. For example, a method of removing abnormal data may be implemented by recording on a computer-readable recording medium a first program for calculating "n" parameters with respect to "n" pulses included in a PPG signal corresponding to the first and second wavelengths, the PPG signal being collected for a predetermined unit period of time; and a second program for calculating an average of the "n" parameters and comparing a ration of the umber of parameters whose deviation from the average is greater than a predetermined standard deviation to the "n" parameters with a predetermined removal reference value so as to determine whether the "n" pulse data is valid. A third program may decide what to do with the data in accordance with the validity determination from the second program, i.e., the branching at step 37 in FIG. 3.

The computer-readable recording medium may be any type of medium on which data that may be read by a computer system may be recorded, for example, a ROM, a RAM, a CD-ROM, a magnetic tape, a floppy disc, or an optical data storage device. The present invention may also be realized as carrier waves (for example, transmitted through Internet). Alternatively, computer-readable recording media are distributed among computer systems connected through a network so that the present invention may be realized as a code stored on the recording media and may be read and executed in the computers. Programmers in the art of the present invention can easily infer functional programs, codes, and code segments for implementing the present invention.

Example

In order to obtain quantitative results of a method of removing abnormal data according to an embodiment of the present invention, data was continuously collected for ten (10) minutes from thirty (30) subjects lying on their back and having a hemoglobin concentration of 10.5-16.5 g/dl. The population composed of thirty (30) subjects was divided at a ratio of 2 to 1, and a regressive equation was obtained through multivariate linear regressive analysis having twenty (20) subjects as a calibration model. The regressive equation was applied to the data collected from the remaining ten (10) subjects to calculate the result for a prediction model. Hemoglobin values of all the subjects to be used as references were measured using HemoCue AB (Sweden), an apparatus for invasively measuring hemoglobin using a cuvette.

In order to determine whether parameters, i.e., RORs between wavelengths, were abnormal data, a standard deviation for a ratio $R_{13}$ of a logarithmic ratio with respect to a wavelength of 569 nm to a logarithmic ratio with respect to a wavelength of 805 nm and a standard deviation for a ratio $R_{45}$ of a logarithmic ratio with respect to a wavelength of 940 nm to a logarithmic ratio with respect to a wavelength of 970 nm were increased by 2% and 1%, respectively. A removal reference value was set to 20%, and a unit period of time for the determination was set to one (1) minute. As the standard deviation was small, a correlation coefficient was high, but the number N of subjects satisfying the standard deviation decreased, not allowing much data to be analyzed. The correlation coefficient was in inverse proportion to the number N of subjects satisfying the standard deviation. Accordingly, the standard deviations for $R_{13}$ and $R_{45}$ were optimally set to 4% and 2%, respectively. Table 2 shows correlation coefficients and the number N of subjects to be analyzed in the calibration model and the prediction model with respect to $R_{13}$ and $R_{45}$.

TABLE 2

| Standard deviation | | Calibration model | | | Prediction model | | |
|---|---|---|---|---|---|---|---|
| | | Correlation coefficient | Standard deviation | Number of subjects | Correlation coefficient | Standard deviation | Number of subjects |
| $R_{13}$ (%) | $R_{45}$ (%) | (R) | (g/dl) | (N) | (R) | (g/dl) | (N) |
| 2 | 1 | 0.71 | 1.2 | 15 | 0.65 | 1.4 | 6 |
| 4 | 2 | 0.71 | 1.3 | 20 | 0.61 | 1.7 | 10 |
| 6 | 3 | 0.59 | 1.5 | 20 | 0.39 | 2.05 | 10 |
| 8 | 4 | 0.53 | 1.82 | 20 | 0.3 | 2.34 | 10 |
| The present invention is not applied | | 0.51 | 1.9 | 20 | 0.3 | 2.4 | 10 |

Referring to Table 2, when a method of removing abnormal data using the optimal standard deviations and the predetermined removal reference value to determine whether the collected data would be used to non-invasively measure a hemoglobin concentration in blood, according to the present invention, was applied to the thirty (30) subjects, a correlation coefficient of 0.71 was obtained with respect to the calibration model, and a correlation coefficient of 0.61 was obtained with respect to the prediction model.

As compared to the results of analysis performed without using a method of the present invention where a correlation coefficient of 0.51 was obtained with respect to the calibration model and a correlation coefficient of 0.3 was obtained with respect to the prediction model, the present invention improved the results of analysis. Accordingly, the present invention is effective at minimizing an influence due to a change in a pulsatile component, whether caused by an internal vital factor, such as breathing, blood pressure, pulse rate, body temperature, a state of blood vessels, or an autonomic nervous system, and/or by an external vital factor, such as motion-induced noise or an unstable contact of a probe, on a physiological signal.

As described above, according to the present invention, a blood component analysis system using spectroscopy calculates parameters of a regressive equation from a PPG signal generated from a subject, analyzes abnormal data of the parameters for a predetermined unit period of time, and excludes a data group including abnormal data whose proportion is equal to or greater than a predetermined removal reference value from the analysis, thereby minimizing influence of a change in a pulsatile component due to an internal vital factor and/or due to an external vital factor. Such external factor influence may be realized without the use of separate hardware systems, such as a motion sensor and an accelerometer, for measuring the external factors. As a result, the accuracy of the analysis may be increased without increasing the manufacturing cost of a blood component analysis system.

Moreover, according to an embodiment of the present invention, time taken for preparing a patient in a stable status required for general test of a physiological signal is eliminated or minimized, so that entire time for analysis may be reduced. In addition, the validity of data may be automatically and objectively determined, as opposed to conventional subjective analysis depending on a tester, so that the accuracy of analysis may be maintained constant.

Embodiments of the present invention have been disclosed herein and, although specific terms are employed, they are used and are to be interpreted in a generic and descriptive sense only and not for purpose of limitation. Accordingly, it will be understood by those of ordinary skill in the art that various changes in form and details may be made without departing from the spirit and scope of the present invention as set forth in the following claims.

What is claimed is:

1. A method of removing abnormal data in a blood component analysis system using spectroscopy to estimate a concentration of a blood component by analyzing a photo-plethysmographic (PPG) signal obtained by radiating light of first and second wavelengths reacting to the blood component on a subject and detecting light corresponding to the first and second wavelengths output from the subject, the method comprising:
    (a) collecting the PPG signal corresponding to the first and second wavelengths for a predetermined unit period of time, the collected PPG signal including "n" pulse data for each of the first and second wavelengths, the "n" pulse data representing a group of n pulses in the PPG signal corresponding to the first wavelength and a group of n pulses in the PPG signal corresponding to the second wavelength, n being a positive integer larger than 1;
    (b) calculating a ratio between a maximum intensity value and a minimum intensity value for each pulse of the "n" pulse data for each of the first and second wavelengths, and obtaining "n" first ratio values corresponding to the n pulses of the first wavelength and "n" second ratio values corresponding to the n pulses of the second wavelength;
    (c) calculating third ratio values between the "n" first ratio values and respective "n" second ratio values, the third ratio values defining "n" parameter values with respect to the "n" pulse data included in the collected PPG signal;
    (d) calculating an average of the "n" parameter values;
    (e) among the "n" parameters, determining a number "m" of parameter values whose deviations from the average calculated in (d) are greater than a predetermined standard deviation, wherein when the first and second wavelengths correspond to an isosbestic point, the predetermined standard deviation is set to ±3.5% through ±4.5%;
    (f) comparing a ratio m/n with a predetermined removal reference value, and determining whether the "n" pulse data is valid; and
    (g) replacing invalid "n" pulse data with new "n" pulse data, the new "n" pulse data being new pulse data in a newly collected PPG signal.

2. The method as claimed in claim 1, further comprising:
    completely removing all the n pulses within the invalid "n" pulse data from the spectroscopy analysis when m/n is equal to or greater than the predetermined removal reference value;
    replacing all of the removed "n" pulse data with newly collected "n" pulse data; and
    repeating steps (b) through (g) for the newly collected "n" pulse data.

3. The method as claimed in claim 1, further comprising:
    dividing the n pulses of each of the first and second wavelengths into "x" unit groups when m/n is equal to or greater than the predetermined removal reference value, each "x" unit group having a predetermined number of pulses larger than 1;
    replacing a first "x" unit group of the "n" pulse data with newly collected data; and
    repeating steps (b) through (g) for the "n" pulse data with the newly collected data.

4. The method as claimed in 1, wherein when the first and second wavelengths are in one of a red range and an infrared range, the standard deviation is set to ±1.5% through ±2.5%.

5. The method as claimed in claim 1, wherein the pulses are modulations in the PPG signal arising from a change in a blood flow caused by an external pressure.

6. The method as claimed in claim 1, further comprising:
    storing the "n" pulse data when the ratio is less than the predetermined removal reference value in step (f).

7. The method as claimed in claim 1, wherein replacing the invalid "n" pulse data includes replacing all the n pulses in the collected PPG signal with new n pulses in a newly collected PPG signal.

8. A tangible, non-transitory computer-readable recording medium in a blood component analysis system using spectroscopy to estimate a concentration of a blood component by analyzing a photo-plethysmographic (PPG) signal obtained by radiating light of first and second wavelengths reacting to the blood component on a subject and detecting light corresponding to the first and second wavelengths output from the subject, wherein execution of code stored in the tangible, non-transitory computer-readable recording medium by one or more processors of a computer system causes the one or more processors to carry out:
    collecting the PPG signal corresponding to the first and second wavelengths for a predetermined unit period of time, the collected PPG signal including "n" pulse data for each of the first and second wavelengths, the "n" pulse data representing a group of n pulses in the PPG signal corresponding to the first wavelength and a group of n pulses in the PPG signal corresponding to the second wavelength, n being a positive integer larger than 1;
    calculating a ratio between a maximum intensity value and a minimum intensity value for each pulse of the "n" pulse data for each of the first and second wavelengths, and obtaining "n" first ratio values corresponding to the n pulses of the first wavelength and "n" second ratio values corresponding to the n pulses of the second wavelength;
    calculating third ratio values between "n" first ratio values and respective "n" second ratio values;

calculating an average of "n" parameters, the "n" parameters being the third ratio values;

among the "n" parameters, determining a number "m" of parameter values, deviations from the average are greater than a predetermined standard deviation, wherein when the first and second wavelengths correspond to an isosbestic point, the predetermined standard deviation is set to ±3.5% through ±4.5%;

comparing a ratio m/n with a predetermined removal reference value to determine whether the "n" pulse data is valid; and replacing invalid "n" pulse data with new "n" pulse data, the new "n" pulse data being new pulse data in a newly collected PPG signal.

9. The tangible, non-transitory computer readable recording medium as claimed in claim 8, wherein the tangible, non-transitory computer-readable recording medium further causes the one or more processors to carry out:

storing "n" pulse data when the "n" pulse data is determined to be valid, and replacing the removed "n" pulse data when the "n" pulse data is determined not to be valid with new "n" pulse data.

10. The tangible, non-transitory computer readable recording medium as claimed in claim 9, wherein all of the "n" pulse data is replaced with new "n" pulse data.

11. The tangible, non-transitory computer readable recording medium as claimed in claim 9, wherein the "n" pulse data is divided into predetermined unit groups, and a first predetermined unit group composed of first input data is replaced with the same amount of newly collected data as the first predetermined unit group.

12. An apparatus for removing abnormal data in a blood component analysis system using spectroscopy to estimate a concentration of a blood component by analyzing a photoplethysmographic (PPG) signal obtained by radiating light of first and second wavelengths reacting to the blood component on a subject and detecting light corresponding to the first and second wavelengths output from the subject, the apparatus comprising:

a signal processor programmed to:

extract the (PPG) signal corresponding to the first and second wavelengths reacting to a particular blood component from an electrical signal output in response to the detected light, the extracted PPG signal including "n" pulse data for each of the first and second wavelengths, the "n" pulse data representing a group of n pulses in the PPG signal corresponding to the first wavelength and a group of n pulses in the PPG signal corresponding to the second wavelength, n being a positive integer larger than 1, calculate a ratio between a maximum intensity value and a minimum intensity value for each pulse of the "n" pulse data of each of the first and second wavelengths, and obtain "n" first ratio values corresponding to the n pulses of the first wavelength and "n" second ratio values corresponding to the n pulses of the second wavelength, calculate third ratio values between the "n" first ratio values and respective "n" second ratio values, the third ratio values defining "n" parameter values with respect to the "n" pulse data included in the collected PPG signal, calculate an average of the "n" parameter values, among the "n" parameter values, to determine a number "m" of parameter values whose deviations from the average are greater than a predetermined standard deviation, wherein when the first and second wavelengths correspond to an isosbestic point, the predetermined standard deviation is set to ±3.5% through ±4.5%, compare m/n with a predetermined removal reference value to determine whether the "n" pulse data is valid, and replace invalid "n" pulse data with new "n" pulse data, the new "n" pulse data being new pulse data in a newly collected PPG signal.

13. The apparatus as claimed in claim 12, wherein the signal processor is programmed to store the "n" pulse data, and when the "n" pulse data is determined as being invalid, to divide the "n" pulse data into predetermined unit groups, to replace a first predetermined unit group composed of first input data with the same amount of new data as the first predetermined unit group, and to determine whether new "n" pulse data is valid.

14. The apparatus as claimed in claim 12, wherein when the first and second wavelengths are in a red range or an infrared range, the standard deviation is set to ±1.5% through ±2.5%.

15. The apparatus as claimed in claim 12, wherein the pulses are modulations in the PPG signal arising from a change in a blood flow caused by an external pressure.

16. The apparatus as claimed in claim 12, further comprising:

a storage unit adapted to store the "n" pulse data determined to be valid.

* * * * *